US010610289B2

(12) United States Patent
Jensen

(10) Patent No.: US 10,610,289 B2
(45) Date of Patent: Apr. 7, 2020

(54) DEVICES, SYSTEMS, AND METHODS FOR GRASPING, TREATING, AND DIVIDING TISSUE

(71) Applicant: COVIDIEN LP, Mansfield, MA (US)

(72) Inventor: Jeffrey L. Jensen, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 1626 days.

(21) Appl. No.: 14/260,905

(22) Filed: Apr. 24, 2014

(65) Prior Publication Data

US 2015/0088122 A1 Mar. 26, 2015

Related U.S. Application Data

(60) Provisional application No. 61/882,046, filed on Sep. 25, 2013.

(51) Int. Cl.
*A61B 18/14* (2006.01)
*A61B 34/30* (2016.01)
*A61B 18/00* (2006.01)

(52) U.S. Cl.
CPC .......... *A61B 18/1445* (2013.01); *A61B 34/30* (2016.02); *A61B 2018/0063* (2013.01);
(Continued)

(58) Field of Classification Search
CPC ................ A61B 18/1445; A61B 34/30; A61B 2018/00607; A61B 2018/0063;
(Continued)

(56) References Cited

U.S. PATENT DOCUMENTS

D249,549 S 9/1978 Pike
D263,020 S 2/1982 Rau, III
(Continued)

FOREIGN PATENT DOCUMENTS

CN 201299462 9/2009
DE 2415263 A1 10/1975
(Continued)

OTHER PUBLICATIONS

U.S. Appl. No. 13/731,674, filed Dec. 31, 2012; inventor: Siebrecht.
(Continued)

*Primary Examiner* — Michael F Peffley
*Assistant Examiner* — Samantha M Good
(74) *Attorney, Agent, or Firm* — Carter, DeLuca & Farrell, LLP

(57) ABSTRACT

A surgical system includes an end effector assembly, a motor assembly, an energy source, and a controller. The controller activates the motor assembly, once it is determined that tissue is present between jaw members of the end effector assembly, to move the jaw members from a spaced-apart position to an approximated position to grasp tissue. The controller further activates the energy source, once tissue is grasped between the jaw members, to supply energy to the jaw members to seal tissue grasped between the jaw members. The controller further activates the motor assembly, once it is determined that tissue sealing is complete, to move the jaw members from the approximated position to the spaced-apart position to release sealed tissue. The system may further be configured to cut tissue once it is determined that tissue sealing is complete but before moving the jaw members to the spaced-apart position.

12 Claims, 12 Drawing Sheets

(52) U.S. Cl.
CPC .............. *A61B 2018/00607* (2013.01); *A61B 2018/00875* (2013.01); *A61B 2018/1452* (2013.01); *A61B 2018/1455* (2013.01)

(58) Field of Classification Search
CPC .. A61B 2018/00875; A61B 2018/1452; A61B 2018/1455
See application file for complete search history.

(56) References Cited

U.S. PATENT DOCUMENTS

| | | | |
|---|---|---|---|
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| 5,480,409 A | 1/1996 | Riza |
| 5,582,611 A | 12/1996 | Tsuruta et al. |
| 5,582,617 A | 12/1996 | Klieman et al. |
| D384,413 S | 9/1997 | Zlock et al. |
| H1745 H | 4/1998 | Paraschac |
| 5,769,791 A | 6/1998 | Benaron et al. |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,909,820 B2 | 3/2011 | Lipson et al. |
| 7,976,544 B2 | 7/2011 | McClurken et al. |
| D649,249 S | 11/2011 | Guerra |
| D649,643 S | 11/2011 | Allen, IV et al. |
| D661,394 S | 6/2012 | Romero et al. |
| 8,277,446 B2 | 10/2012 | Heard |
| D670,808 S | 11/2012 | Moua et al. |
| D680,220 S | 4/2013 | Rachlin |
| 2008/0009860 A1 | 1/2008 | Odom |
| 2009/0204114 A1 | 8/2009 | Odom |
| 2010/0217264 A1 | 8/2010 | Odom et al. |
| 2012/0116391 A1* | 5/2012 | Houser .............. A61B 18/1442 606/41 |
| 2012/0248167 A1* | 10/2012 | Flanagan ......... A61B 17/07207 227/2 |
| 2013/0253489 A1 | 9/2013 | Nau, Jr. et al. |
| 2014/0142574 A1 | 5/2014 | Heard |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |

(56) References Cited

FOREIGN PATENT DOCUMENTS

| | | | |
|---|---|---|---|
| JP | 2001-190564 | A | 7/2001 |
| JP | 2002-136525 | A | 5/2002 |
| JP | 2002-528166 | A | 9/2002 |
| JP | 2003-116871 | A | 4/2003 |
| JP | 2003-175052 | A | 6/2003 |
| JP | 2003245285 | A | 9/2003 |
| JP | 2004-517668 | A | 6/2004 |
| JP | 2004-528869 | A | 9/2004 |
| JP | 2005-152663 | A | 6/2005 |
| JP | 2005-253789 | A | 9/2005 |
| JP | 2005312807 | A | 11/2005 |
| JP | 2006-015078 | A | 1/2006 |
| JP | 2006-501939 | A | 1/2006 |
| JP | 2006-095316 | A | 4/2006 |
| JP | 2008-054926 | A | 3/2008 |
| JP | 2011125195 | A | 6/2011 |
| SU | 401367 | A1 | 11/1974 |
| WO | 0036986 | A1 | 6/2000 |
| WO | 0059392 | A1 | 10/2000 |
| WO | 0115614 | A1 | 3/2001 |
| WO | 0154604 | A1 | 8/2001 |
| WO | 0245589 | A3 | 9/2002 |
| WO | 06/021269 | A1 | 3/2006 |
| WO | 05110264 | A3 | 4/2006 |
| WO | 08/040483 | A1 | 4/2008 |
| WO | 2011/018154 | A1 | 2/2011 |

OTHER PUBLICATIONS

U.S. Appl. No. 14/065,644, filed Oct. 29, 2013; inventor: Reschke.
U.S. Appl. No. 14/098,953, filed Dec. 6, 2013; inventor: Cunningham.
U.S. Appl. No. 14/100,237, filed Dec. 9, 2013; inventor: Reschke.
U.S. Appl. No. 14/103,971, filed Dec. 12, 2013; inventor: Roy.
U.S. Appl. No. 14/105,374, filed Dec. 13, 2013; inventor: Moua.
U.S. Appl. No. 14/152,618, filed Jan. 10, 2014; inventor: Artale.
U.S. Appl. No. 14/152,690, filed Jan. 10, 2014; inventor: Hart.
U.S. Appl. No. 14/169,358, filed Jan. 31, 2014; inventor: Reschke.
U.S. Appl. No. 14/173,391, filed Feb. 5, 2014; inventor: Kharin.
U.S. Appl. No. 14/176,341, filed Feb. 10, 2014; inventor: Hart.
U.S. Appl. No. 14/177,812, filed Feb. 11, 2014; inventor: Dycus.
U.S. Appl. No. 14/182,894, filed Feb. 18, 2014; inventor: Hart.
U.S. Appl. No. 14/182,967, filed Feb. 18, 2014; inventor: Latimer.
U.S. Appl. No. 14/183,090, filed Feb. 18, 2014; inventor: Arts.
U.S. Appl. No. 14/196,066, filed Mar. 4, 2014; inventor: McCullough.
U.S. Appl. No. 14/250,180, filed Apr. 10, 2014; inventor: Guerra.
U.S. Appl. No. 14/253,017, filed Apr. 15, 2014; inventor: Orszulak.
U.S. Appl. No. 14/260,905, filed Apr. 24, 2014; inventor: Jensen.
U.S. Appl. No. 14/268,051, filed May 2, 2014; inventor: Hart.
U.S. Appl. No. 14/268,140, filed May 2, 2014; inventor: Twomey.
U.S. Appl. No. 14/273,350, filed May 8, 2014; inventor: Gilbert.
U.S. Appl. No. 14/274,445, filed May 9, 2014; inventor: Hixson.
U.S. Appl. No. 14/276,465, filed May 13, 2014; inventor: Kappus.
U.S. Appl. No. 14/282,738, filed May 20, 2014; inventor: Rachlin.
U.S. Appl. No. 14/284,618, filed May 22, 2014; inventor: Hempstead.
U.S. Appl. No. 14/286,105, filed May 23, 2014; inventor: Johnson.
U.S. Appl. No. 14/294,316, filed Jun. 3, 2014; inventor: Johnson.
U.S. Appl. No. 14/295,049, filed Jun. 3, 2014; inventor: Couture.
U.S. Appl. No. 14/295,730, filed Jun. 4, 2014; inventor: Sartor.
U.S. Appl. No. 14/295,757, filed Jun. 4, 2014; inventor: McKenna.
U.S. Appl. No. 14/297,316, filed Jun. 5, 2014; inventor: Ackley.
U.S. Appl. No. 14/297,404, filed Jun. 5, 2014; inventor: Allen.
U.S. Appl. No. 14/299,740, filed Jun. 9, 2014; inventor: Larson.
U.S. Appl. No. 14/319,869, filed Jun. 30, 2014; inventor: Cunningham.
U.S. Appl. No. 14/322,513, filed Jul. 2, 2014; inventor: Duffin.
U.S. Appl. No. 14/335,303, filed Jul. 18, 2014; inventor: Lee.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal hysterectomy" Obstetrics & Gynecology, vol. 102, No. 1, Jul. 2003.

(56) References Cited

OTHER PUBLICATIONS

"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997; inventor: James G. Chandler.
U.S. Appl. No. 09/177,950, filed Oct. 23, 1998; inventor: Randel A. Frazier.
U.S. Appl. No. 09/387,883, filed Sep. 1, 1999; inventor: Dale F. Schmaltz.
U.S. Appl. No. 09/591,328, filed Jun. 9, 2000; inventor: Thomas P. Ryan.
U.S. Appl. No. 12/336,970, filed Dec. 17, 2008; inventor: Paul R. Sremcich.

\* cited by examiner

DEVICES, SYSTEMS, AND METHODS FOR GRASPING, TREATING, AND DIVIDING TISSUE

CROSS REFERENCE TO RELATED APPLICATION

The present application claims the benefit of and priority to U.S. Provisional Application Ser. No. 61/882,046, filed on Sep. 25, 2013, the entire contents of which are incorporated herein by reference.

BACKGROUND

Technical Field

The present disclosure relates to surgical devices and systems and, more particularly, to surgical forceps and systems capable of rapidly and repeatedly grasping, treating, and dividing tissue.

Background of Related Art

A surgical forceps is a plier-like device which relies on mechanical action between its jaws to grasp, clamp, and constrict tissue. Energy-based surgical forceps utilize both mechanical clamping action and energy to affect hemostasis by heating tissue to coagulate and/or cauterize tissue. Certain surgical procedures require more than simply cauterizing tissue and rely on the unique combination of clamping pressure, precise energy control and gap distance (i.e., distance between opposing jaw members when closed about tissue) to "seal" tissue. Typically, once tissue is sealed, the surgeon has to accurately sever the tissue along the newly formed tissue seal. Accordingly, many tissue sealing devices have been designed which incorporate a knife or blade member which effectively severs the tissue after forming a tissue seal. More recently, tissue sealing devices have incorporated energy-based cutting features for energy-based tissue division.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with the present disclosure, a surgical system is provided generally including an end effector assembly, a motor assembly, an energy source, and a controller. The end effector assembly includes first and second jaw members. The motor assembly is coupled to the end effector assembly and is operable to move the jaw members between a spaced-apart position and an approximated position for grasping tissue therebetween. The energy source is coupled to the end effector assembly and is operable to supply energy to the jaw members to seal tissue. The controller includes a processor and a non-transitory computer-readable storage medium storing a control program. The control program, when executed, causes the processor to: activate the motor assembly, once it is determined that tissue is present between the jaw members, to move the jaw members from the spaced-apart position to the approximated position to grasp tissue; activate the energy source, once tissue is grasped between the jaw members, to supply energy to the jaw members to seal tissue grasped between the jaw members; and activate the motor assembly, once it is determined that tissue sealing is complete, to move the jaw members from the approximated position to the spaced-apart position to release sealed tissue.

In aspects of the present disclosure, a forceps having the end effector assembly disposed at a distal end thereof is provided and/or a generator containing the energy source and the controller is provided. In aspects, the generator is operably coupled to the forceps. Further, the generator may be incorporated into a housing of the forceps.

In aspects of the present disclosure, one or more first sensors is coupled to the end effector assembly and is configured for sensing the presence of tissue between the jaw members. The one or more first sensors is also coupled to the controller for enabling the controller to determine whether tissue is present between the jaw members.

In aspects of the present disclosure, one or more second sensors is coupled between the end effector assembly and the energy source and is configured for sensing one or more tissue properties indicative of completion of tissue sealing. The one or more second sensors is also coupled to the controller for enabling the controller to determine whether tissue sealing is complete. In particular aspects, the one or more of the tissue properties is tissue impedance. Alternatively or additionally, the controller may implement an algorithm for determining whether tissue sealing is complete based upon data received from the energy source, e.g., current, voltage, power, and/or impedance.

In aspects of the present disclosure, the end effector assembly further includes a cutting member that is coupled to the energy source such that the energy source is operable to supply energy to the cutting member for conduction between the cutting member and one or both of the jaw members and through tissue grasped between the jaw members to cut tissue. In such aspects, the control program further causes the processor to activate the energy source, once it is determined that tissue sealing is complete, to supply energy to the cutting member to cut sealed tissue, and activating the motor assembly to move the jaw members from the approximated position to the spaced-apart position to release tissue is effected once it is determined that both tissue sealing and tissue cutting are complete. As an alternative to energy-based cutting, the control program may be configured to cause the processor to activate the motor assembly for advancing a mechanical cutter to cut sealed tissue once it is determined that tissue sealing is complete, as detailed below in other aspects.

In aspects of the present disclosure, the end effector assembly includes a knife movable between a retracted position, wherein the knife is disposed proximally of the jaw members, and an extended position, wherein the knife extends between the jaw members to cut tissue disposed therebetween. The motor assembly is coupled to the knife and is operable to move the knife between the retracted position and the extended position. In such aspects, the control program further causes the processor to activate the motor assembly, once tissue sealing is complete, to move the knife from the retracted position to the extended position to cut sealed tissue, and activating the motor assembly to move the jaw members from the approximated position to the spaced-apart position to release tissue is effected once it is determined that tissue sealing is complete and once tissue cutting is complete.

BRIEF DESCRIPTION OF THE DRAWINGS

Various aspects and features of the present disclosure are described herein with reference to the drawings wherein.

DETAILED DESCRIPTION

Figure 1:
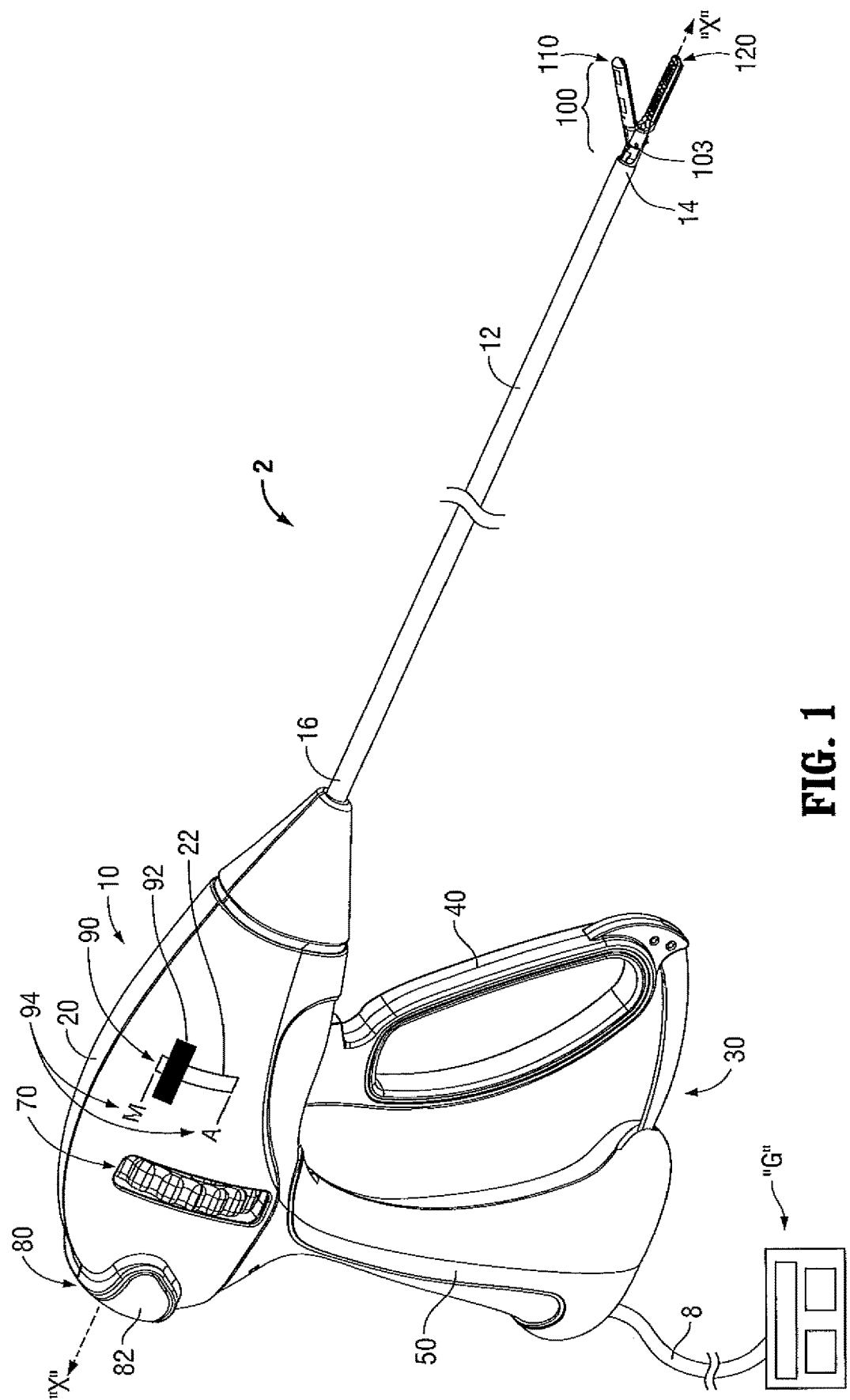
FIG. 1 is a perspective view of a surgical system provided in accordance with the present disclosure.

Turning to FIG. 1, a surgical system provided in accordance with the present disclosure is shown generally identified by reference numeral 2. Surgical system 2 includes a forceps 10 coupled to a generator "G." Forceps 10 is configured for use in connection with traditional open and/or endoscopic surgical procedures, although it is contemplated that any other suitable surgical instrument be utilized as an alternative or in addition to forceps 10 as part of surgical system 2. Obviously, different electrical and mechanical connections and considerations apply to each particular type of instrument, however, the aspects and features of the present disclosure remain generally consistent regardless of the particular instrument used. As will be detailed below, surgical system 2 and, in particular, forceps 10 thereof, is configured for use in both a manual mode, enabling selective manual actuation of forceps 10 for grasping, treating, and/or cutting tissue, and an automatic mode, enabling grasping, treating, cutting, and release of tissue to be automatically and repeatedly effected via feedback-based control. Various other embodiments of surgical systems and/or forceps configured for use the automatic and manual modes are likewise detailed below.

Figure 2A:
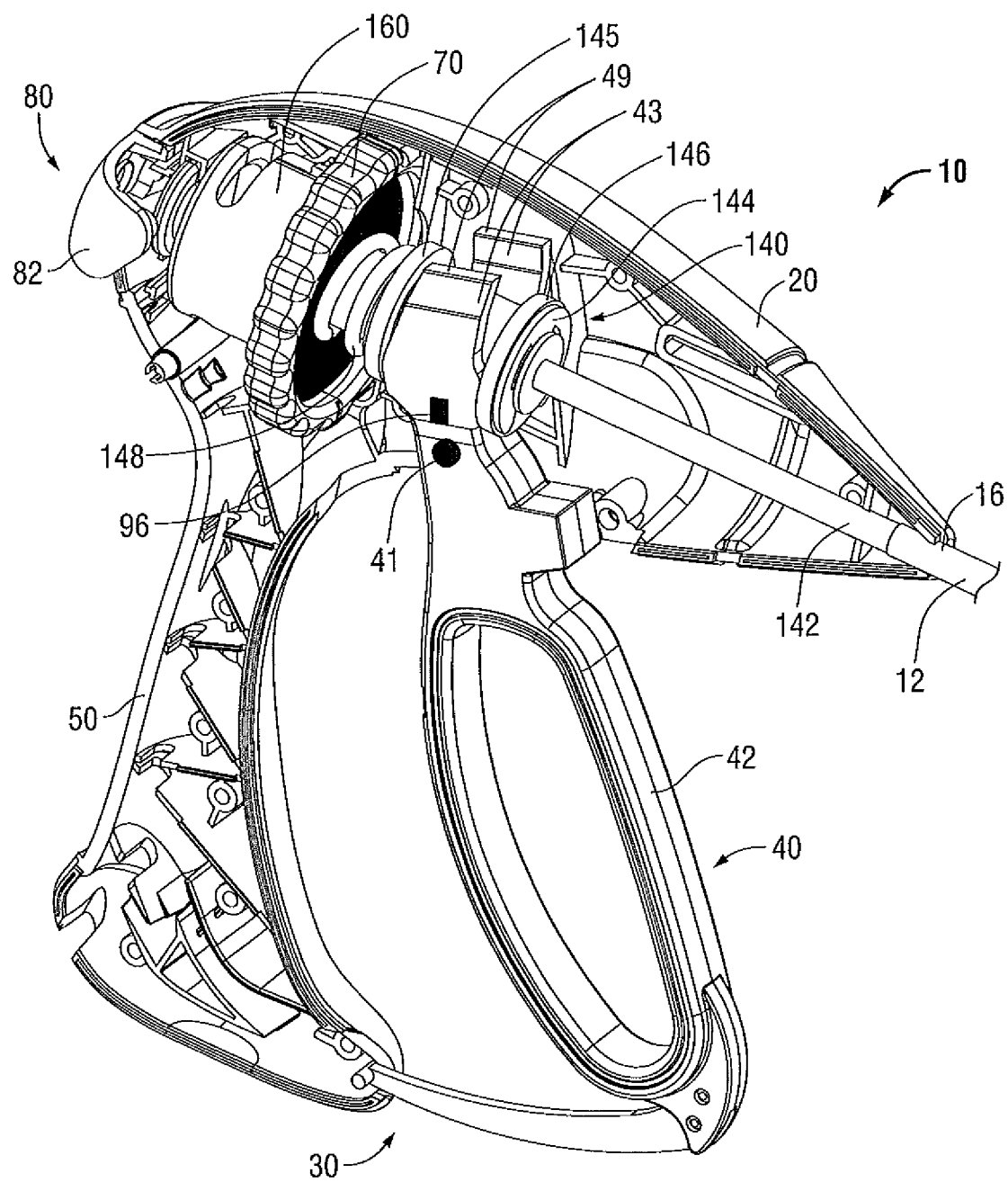
FIG. 2A is a perspective view of the proximal end of the forceps of the surgical system of FIG. 1, wherein a portion of the housing has been removed to show the internal components thereof.
Figure 2B:
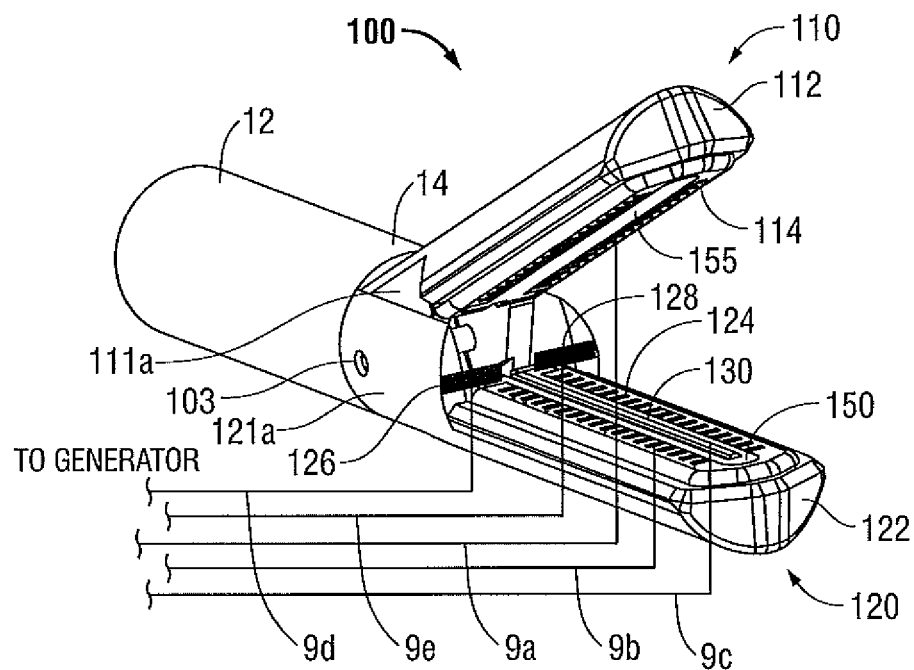
FIG. 2B is a perspective view of the end effector assembly disposed at the distal end of the forceps of the surgical system of FIG. 1, which schematically shows the wiring to the generator of the end effector.
Figure 2C:
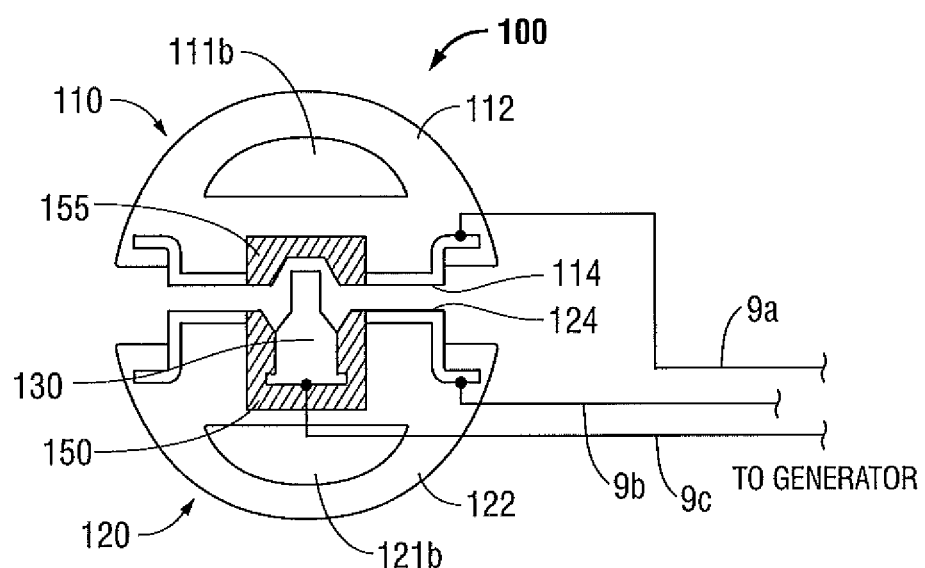
FIG. 2C is a transverse, cross-sectional view of the end effector assembly of FIG. 2B.

Referring to FIGS. 1-2C, forceps 10 defines a longitudinal axis "X" and includes a housing 20, a handle assembly 30, a rotating assembly 70, an activation assembly 80, a selector assembly 90, and an end effector assembly 100. Forceps 10 further includes a shaft 12 having a distal end 14 configured to mechanically engage end effector assembly 100 and a proximal end 16 that mechanically engages housing 20. A cable 8 connects forceps 10 to generator "G" although forceps 10 may alternatively be configured to wirelessly couple to generator "G." As will be detailed below, cable 8 houses a plurality of wires including wires 9a, 9b, 9c, 9d, and 9e (shown schematically in FIG. 2B) that extend through forceps 10 to couple generator "G" to the various components of forceps 10 in order to provide energy and/or control signals to the various components of forceps 10. Activation assembly 80 includes an activation switch 82 provided on housing 20 that may be configured as an on/off switch, e.g., for selectively initiating and deactivating forceps 10 when used in the automatic mode, and/or as a multi-stage switch, e.g., for selectively supplying energy to jaw members 110, 120 of end effector assembly 100 for treating (e.g., sealing) tissue in a first stage and for energy-based tissue cutting in a second stage, when used in the manual mode.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly 140 (FIG. 2A) that, together, mechanically cooperate to impart movement of jaw members 110, 120 between a spaced-apart position and an approximated position to grasp tissue between jaw members 110, 120 when forceps 10 is operating in the manual mode. More specifically, in the manual mode, movable handle 40 is initially spaced-apart from fixed handle 50 and, correspondingly, jaw members 110, 120 are disposed in the spaced-apart position (see FIG. 2A). Movable handle 40 is operable from this initial position to an approximated position corresponding to the approximated position of jaw members 110, 120. Selector assembly 90, as will be detailed below, includes a toggle member 92 provided on housing 20 that allows selection between the manual mode of operation and the automatic mode of operation. Indicia 94, e.g., "A" for automatic and "M" for manual (or other suitable indicia), are provided on housing 20 to indicate the position of toggle member 92 and, thus, the current operating mode of forceps 10. Rotating assembly 70 is rotatable in either direction about longitudinal axis "X" to rotate end effector assembly 100 about longitudinal axis "X."

Referring in particular to FIGS. 2B and 2C, end effector assembly 100 of forceps 10 (FIG. 1) is shown including a pair of jaw members 110, 120. Each jaw member 110, 120 of end effector assembly 100 includes a proximal flange portion 111a, 121a, a distal jaw portion 111b, 121b, an outer insulative jaw housing 112, 122, and a tissue-contacting plate 114, 124, respectively. Proximal flange portions 111a, 121a of jaw members 110, 120 are pivotably coupled to one another about pivot 103 to permit pivoting of one or both of jaw members 110, 120 between the spaced-apart and approximated positions. One or both of proximal flange portions 111a, 121a of jaw members 110, 120 are also coupled to drive bar 142 of drive assembly 140 (FIG. 2A), which is slidably disposed within shaft 12 (FIG. 2A) and is configured to reciprocate relative thereto to effect pivoting of jaw members 110, 120 between the spaced-apart and approximated positions. More specifically, drive bar 142 (FIG. 2A) is pivotably engaged to proximal flange portion 111a of jaw member 110 at a position offset relative to pivot 103 such that distal translation of drive bar 142 (FIG. 2A) urges jaw member 110 to rotate in a first direction about pivot 103 relative to jaw member 120, e.g., from the spaced-apart position towards the approximated position, and such that proximal translation of drive bar 142 (FIG. 2A) pulls jaw member 110 to rotate about pivot 103 in the opposite direction, e.g., from the approximated position towards the spaced-apart position. The reverse configuration, e.g., wherein proximal translation of drive bar 142 (FIG. 2A) effects approximation of jaw members 110, 120 and wherein distal translation of drive bar 142 (FIG. 2A) opens jaw members 110, 120, or other suitable drive mechanisms are also contemplated.

Distal jaw portions 111b, 121b of jaw members 110, 120 are configured to support jaw housings 112, 122, and tissue-contacting plates 114, 124, respectively, thereon. Further, one of the jaw members 110, 120, e.g., jaw members 120, includes an energy-based cutting member 130 disposed thereon. Tissue-contacting plates 114, 124 are formed from an electrically-conductive material, e.g., for conducting energy such as electrosurgical energy therebetween for treating tissue, although tissue-contacting plates 114, 124 may alternatively be configured to conduct any suitable energy through tissue grasped therebetween for energy-based tissue treatment, e.g., tissue sealing. Energy-based cutting member 130 is likewise formed from an electrically conductive material, e.g., for conducting energy such as electrosurgical energy between energy-based cutting member 130 and one or both of tissue-contacting plates 114, 124 for electrically cutting tissue, although energy-based cutting member 130 may alternatively be configured to conduct any suitable energy through tissue for cutting tissue.

Tissue-contacting plates 114, 124 are coupled to activation switch 82 (FIG. 1) and generator "G" (FIG. 1) or other suitable source of energy, e.g., via wires 9a and 9b, respectively, such that electrosurgical energy may be selectively supplied to tissue-contacting plate 114 and/or tissue-contacting plate 124 and conducted therebetween and through tissue disposed between jaw members 110, 120 to treat, e.g., seal, tissue. Wires 9a and 9b and tissue-contacting plates 114, 124 also cooperate with tissue property unit 844 of sensor module 840 of generator "G" (FIG. 9) to allow for sensing of various parameters of tissue grasped between jaw members 110, 120 such as tissue impedance. Alternatively, the tissue property sensor may be disposed within either or both of jaw members 110, 120.

Cutting member 130 is similarly coupled to activation switch 82 (FIG. 1) and generator "G" (FIG. 1) via a wire 9c such that electrosurgical energy may be selectively supplied to cutting member 130 and conducted through tissue disposed between jaw members 110, 120 to either or both of tissue-contacting plates 114, 124 to cut tissue. Wire 9c and cutting member 130, in conjunction with wires 9a, 9b and tissue-contacting plates 114, 124, also cooperate with tissue property unit 844 of sensor module 840 of generator "G" (FIG. 9) to allow for sensing of tissue impedance and/or other parameters of tissue grasped between jaw members 110, 120. A first insulating member 150 surrounds cutting member 130 to insulate tissue-contacting plate 124 and cutting member 130 from one another. A second insulating member 155 disposed within a longitudinal slot defined within tissue-contacting plate 114 of jaw member 110 opposes cutting member 130 to insulate cutting member 130 from tissue-contacting plate 114 of jaw member 110 when jaw members 110, 120 are disposed in the approximated position.

One or both of jaw members 110, 120 further includes one or more tissue presence sensors 126, 128 configured to detect the presence of tissue between jaw members 110, 120 and/or the position of tissue disposed between jaw members 110, 120. Sensors 126, 128 are shown disposed on proximal flange portion 121a of jaw member 120, although sensors 126, 128 may be disposed in any suitable position on jaw member 110 and/or jaw member 120 for sensing the presence and/or position of tissue therebetween. In particular, it is envisioned that sensors 126, 128 alternatively be incorporated into or disposed adjacent to tissue-contacting plates 114, 124 of jaw members 110, 120. Sensors 126, 128 may be any suitable sensors, such as optical distancers, laser distancers, LED distancers, ultrasonic distancers, acoustic distancers, infrared distancers, RF distances, and the like. Distancers operate by bouncing energy, e.g., light, sound, etc., from an opposing surface and measuring the duration of the energy travel back to the sensor or sensors, thus allowing the determination of whether and/or where tissue is disposed between jaw members 110, 120. Wires 9d and 9e couple sensors 126, 128 to tissue presence unit 842 of sensor module 840 of generator "G" (FIG. 9), for feedback-based control of end effector assembly 100, as will be detailed below. Other suitable sensors are also contemplated.

With reference to FIGS. 1 and 2A, the various operable components and features of forceps 10 that cooperate to permit use of forceps 10 in the manual mode of operation are described. Forceps 10 includes a movable handle 40 that is pivotably coupled to housing 20 via a pivot pin 41. A grasping portion 42 of movable handle 40 extends downwardly from pivot pin 41 to facilitate grasping and manipulation of movable handle 40. Movable handle 40 further includes first and second flanges 43 that extend upwardly from pivot pin 41 into housing 20. More specifically, first and second flanges 43 extend on either side of a mandrel 144 disposed about drive bar 142 and between proximal and distal rims 145, 146, respectively, of mandrel 144. Mandrel 144 is fixedly engaged to drive bar 142 such that, as movable handle 40 is pivoted about pivot pin 41 from the initial position towards the depressed position, flanges 43 contact distal rim 146 mandrel 144 to urge drive bar 142 distally. On the other hand, as movable handle 40 is returned towards the initial position, flanges 43 contact proximal rim 145 of mandrel 144 and urge drive bar 142 proximally. As mentioned above, drive bar 142 is coupled to jaw member 110 such that distal translation of drive bar 142 rotates jaw member 110 from the spaced-apart position towards the approximated position, while proximal translation of drive bar 142 rotates jaw member 110 from the approximated position back towards the spaced-apart position. Thus, jaw members 110, 120 are pivoted between the spaced-apart and approximated positions upon pivotable movement of movable handle 40 between the initial and depressed positions when forceps 10 is operating in the manual mode. Drive assembly 140 may further include a biasing member 148 for biasing jaw members 110, 120 towards the approximated position.

Figure 3A:
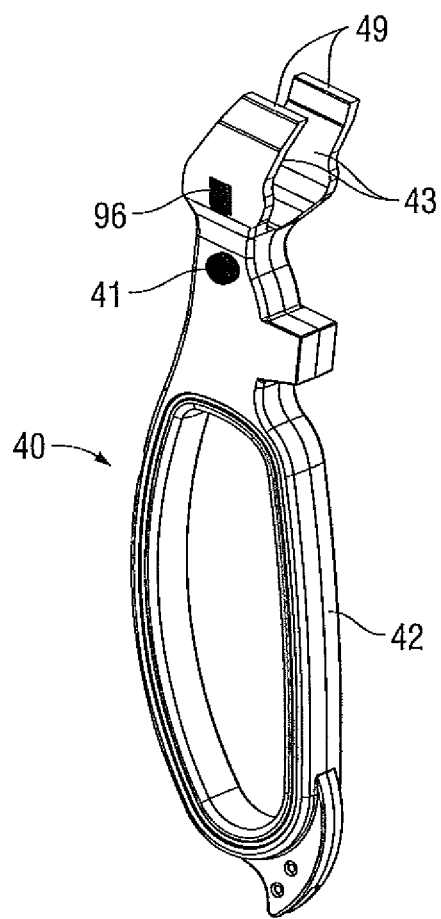
FIG. 3A is a perspective view of the movable handle of the forceps of the surgical system of FIG. 1 disposed in an enabled condition.
Figure 3B:
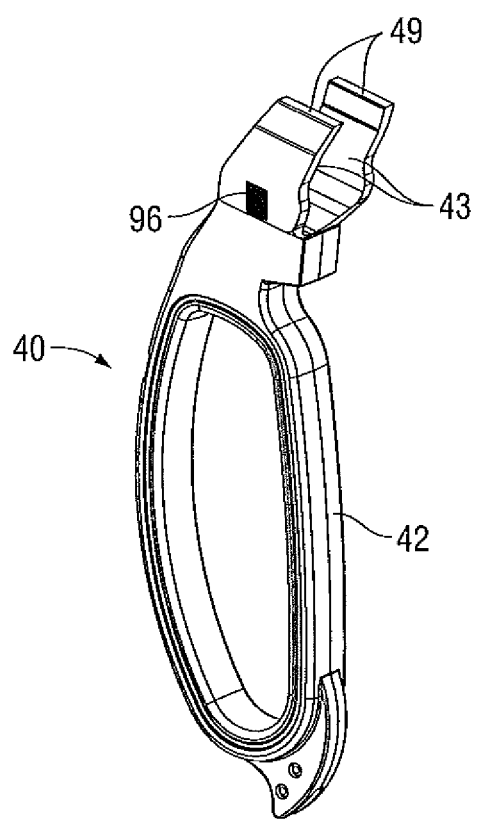
FIG. 3B is a perspective view of the movable handle of FIG. 3A disposed in a disabled condition.

With additional reference to FIGS. 3A-3B, in conjunction with FIGS. 1 and 2A, as mentioned above, forceps 10 further includes a selector assembly 90 having a toggle member 92 provided on either side of housing 20 that allows for selection between the manual mode of operation and the automatic mode of operation. More specifically, selector assembly 90 includes a base 96 coupled to each of flanges 43 of movable handle 40. A toggle member 92 extend from each base 92 though a slot 22 defined within housing 20, thus allowing manual manipulation of toggle member 92. Flanges 43 are configured as telescoping components movable between extended positions (FIG. 3A) and retracted positions (FIG. 3B). Selector assembly 90 and/or flanges 43 may include spring-pin, friction-fit, latching, or other suitable releasable engagement mechanisms for releasably retaining flanges 43 in the extended and retracted positions (FIGS. 3A and 3B, respectively). Selector assembly 90 may be electrically coupled to generator "G" and/or motor assembly 160 for communicating the position of toggle member 92, thus allowing surgical system 2 to ascertain the mode of operation of forceps 10.

In the extended position of flanges 43, corresponding to the manual mode of operation of forceps 10, as shown in FIGS. 2A and 3A, flanges 43 are operably engaged to mandrel 144 between proximal and distal rims 145, 146, respectively, thereof, thus operably coupling movable handle 40 and drive assembly 140 to one another. In the retracted position of flanged 43, on the other hand, telescoping portions 49 of flanges 43 are displaced and disengaged from mandrel 144 such that movable handle 40 is no longer engaged to drive assembly 140, rendering movable handle 40 inoperable.

Referring again to FIGS. 1 and 2A, forceps 10 further includes a motor assembly 160 disposed within housing 20 and operably coupled to the proximal end of drive bar 142. Motor assembly 160 is powered and controlled by generator "G," or other suitable power source, e.g., via one or more of the wires extending through cable 8 and forceps 10. When forceps 10 is operating in the automatic mode, motor assembly 160, under the control of generator "G," is utilized to translate drive bar 142 through shaft 12 and relative to end effector assembly 100 to pivot jaw members 110, 120 between the spaced-apart and approximated positions. Various embodiments of motor assemblies suitable for this purpose are described below with respect to FIGS. 8A and 8B.

Turning to FIGS. 4A-4E, another embodiment of a forceps provided in accordance with the present disclosure is shown generally identified by reference numeral 210. Forceps 210 is similar to forceps 10 (FIG. 1) and, thus, only the differences therebetween will be described in detail below for purposes of brevity. Further, unless specifically contradicted, forceps 210 may incorporate any of the features of forceps 10 (FIG. 1), and vice versa.

Forceps 210 includes a housing 220, a handle assembly 230, a rotating assembly 270, an activation assembly 280, a trigger assembly 290, and an end effector assembly 2100. Shaft 212 of forceps 210 extends between and interconnects housing 220 and end effector assembly 2100. Forceps 210 may be configured for use as part of a surgical system, e.g., in conjunction with a generator such as generator "G" (FIG. 1).

End effector assembly 2100 includes a pair of opposing jaw members 2110, 2120. Each of jaw members 2110, 2120 includes an electrically-conductive tissue-contacting plate 2114, 2124, respectively. A knife assembly 2180 is disposed within shaft 212 and a knife channel 2115, 2125 is defined within one or both jaw members 2110, 2120 to permit reciprocation of a knife 2184 therethrough, e.g., upon actuation of trigger 292 of trigger assembly 290. That is, rather than providing an electrical cutting member 130 as in end effector assembly 100 of forceps 10 (FIGS. 1-2C), end effector assembly 2100 and forceps 210 incorporate a mechanical knife assembly 2180.

Knife assembly 2180 includes a knife 2184 and a knife bar 2186. Knife 2184 is coupled to knife bar 2186 and extends distally from knife bar 2186 to define a tissue-cutting surface 2188. In use, once jaw members 2110, 2120 have been pivoted from the spaced-apart position (FIG. 4C) to the approximated position (FIG. 4D) to grasp tissue therebetween, and, if desired, after tissue sealing, knife 2184 may be advanced from the retracted position (FIG. 4D) to the extended position (FIG. 4E), e.g., via activation of trigger 292, such that knife 2184 is translated through knife channels 2115, 2125 of jaw members 2110, 2120, respectively, to cut tissue grasped between jaw members 2110, 2120.

Figure 4A:
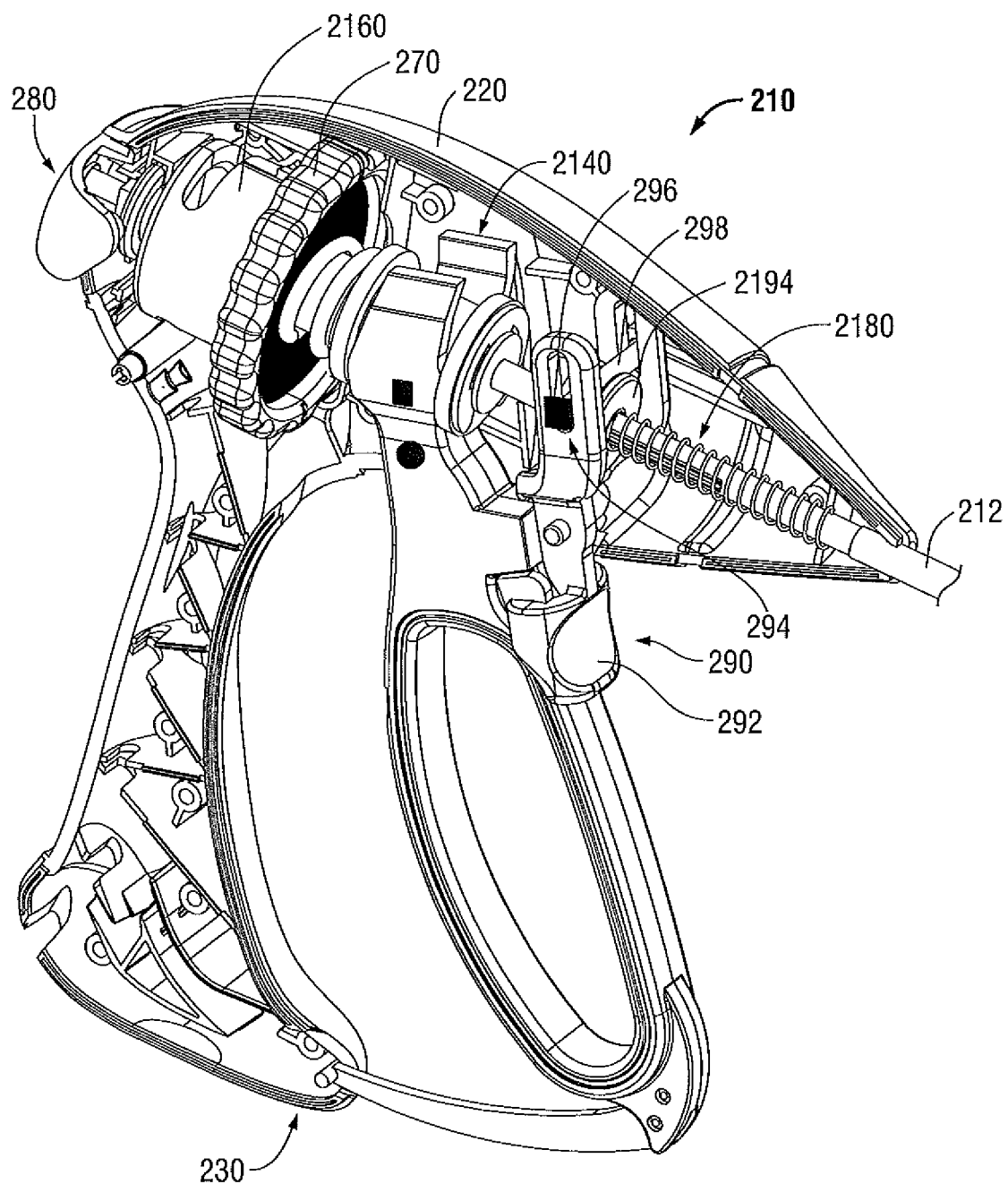
FIG. 4A is a perspective view of the proximal end of another forceps provided in accordance with the present disclosure, wherein a portion of the housing has been removed to show the internal components thereof.
Figure 4B:
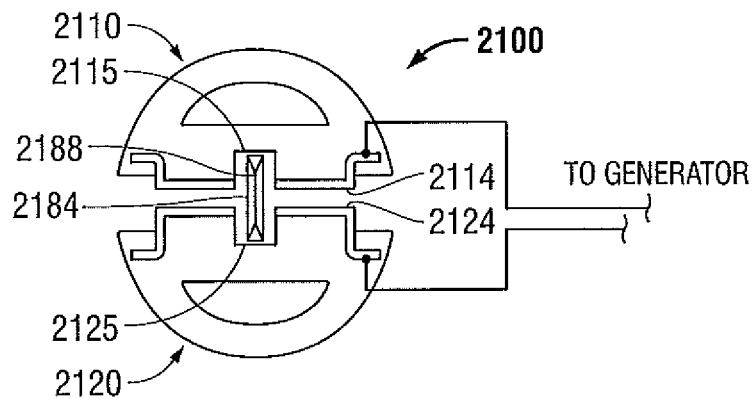
FIG. 4B is a transverse, cross-sectional view of the end effector assembly of the forceps FIG. 4A.
Figure 4C:
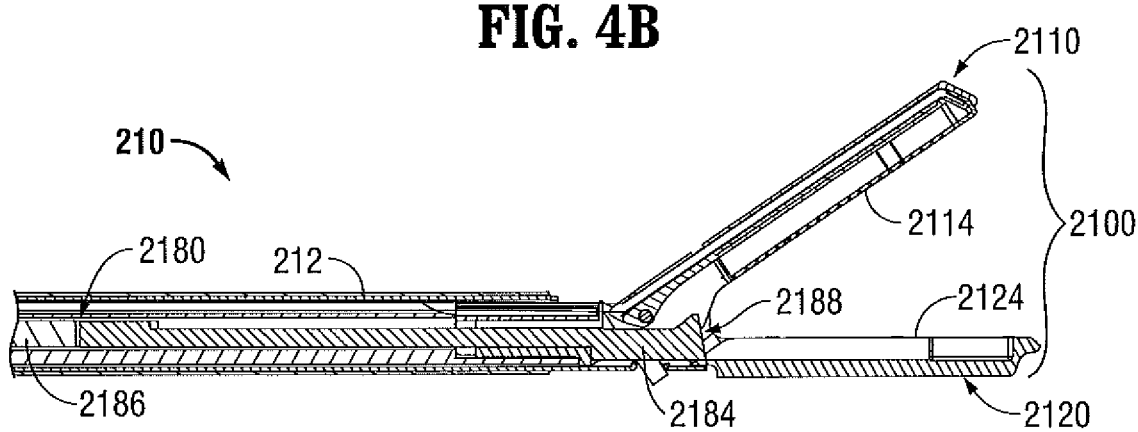
FIG. 4C is a longitudinal, cross-sectional view of the distal end of the forceps of FIG. 4A, wherein the jaw members of the end effector assembly are disposed in a spaced-apart position.
Figure 4D:
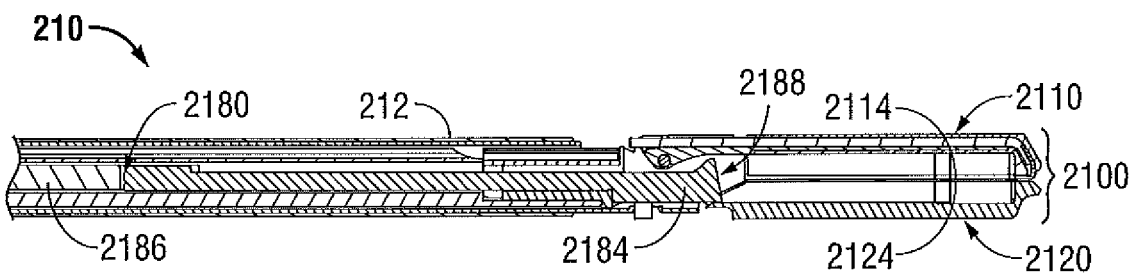
FIG. 4D is a longitudinal, cross-sectional view of the distal end of the forceps of FIG. 4A, wherein the jaw members are disposed in an approximated position and wherein the knife assembly is disposed in a retracted position.
Figure 4E:
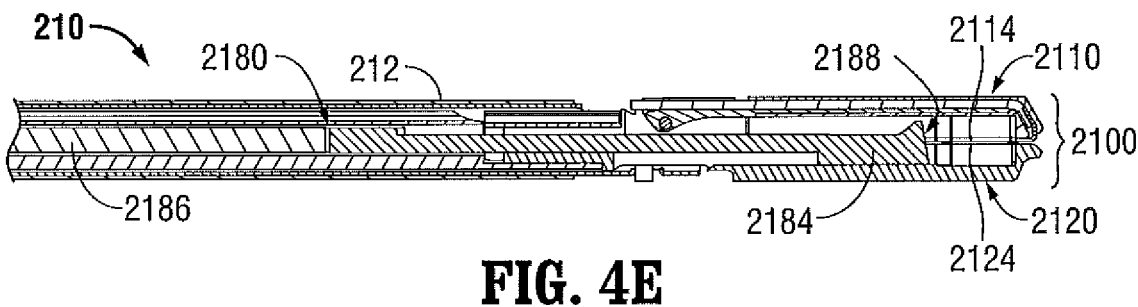
FIG. 4E is a longitudinal, cross-sectional view of the distal end of the forceps of FIG. 4A, wherein the jaw members are disposed in the approximated position and wherein the knife assembly is disposed in a deployed position.

Forceps 210 may additionally include a second selector assembly 294 that, similar to selector assembly 90 of forceps 10 (FIG. 1), includes a toggle member (not shown, similar to toggle member 92 (FIG. 1)) provided on housing 220 for selecting between the manual and automatic modes of operation. However, rather than engaging/disengaging the handle assembly, second selector assembly 294 is provided for selectively engaging/disengaging trigger assembly 290. More specifically, base 296 of second selector assembly 294 is engaged to pin 298, which couples trigger assembly 290 and knife assembly 2180 to one another. As such, with the toggle member (not shown) disposed in the manual position corresponding to the manual mode of operation, as shown in FIG. 4A, pin 298 is coupled to knife bar 2186 via mandrel 2188 such that actuation of trigger 292 effects longitudinal translation of knife bar 2186 and, thus, advancement of knife 2184 from the retracted position to the extended position to cut tissue grasped between jaw members 2110, 2120. Moving the toggle member not shown) to the automatic position corresponding to the automatic mode of operation, on the other hand, disengages pin 298 from mandrel 2194 to thereby decouple trigger assembly 290 from knife assembly 2180, rendering trigger 292 inoperable.

Indicia (not shown, similar to indicia 94 (FIG. 1)) may also be provided for indicating the relative position of second selector assembly 294. Further, rather than providing a second selector assembly 294, a single selector assembly including a toggle member (not shown) operably coupled to both handle assembly 230 and trigger assembly 290 for effecting concurrent engagement or disengagement of handle assembly 230 and trigger assembly 290 from drive assembly 2140 and knife assembly 2180, respectively, may be provided.

Forceps 210 further includes a motor assembly 2160 disposed within housing 220 and operably coupled, independently, to both drive assembly 2140 and knife assembly 2180. Motor is powered and controlled by an energy source, e.g., generator "G-" (FIG. 1), and is configured for effecting pivoting of jaw members 2110, 2120 between the spaced-apart and approximated positions and/or for extending and retracting knife 2184. Various embodiments of motor assemblies suitable for this purpose will be described below with respect to FIGS. 8A and 8B.

Figure 5:
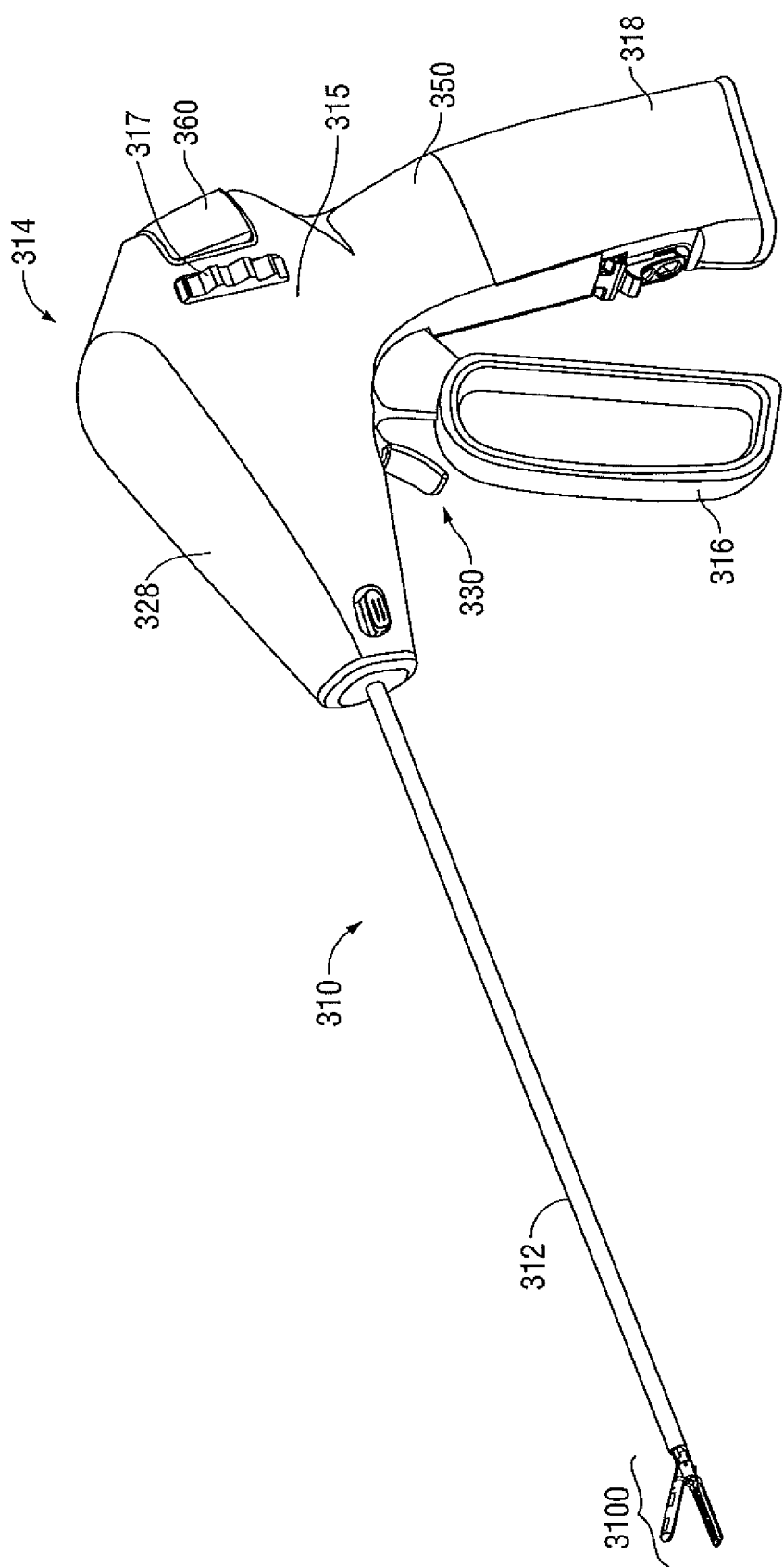
FIG. 5 is a perspective view of another forceps provided in accordance with the present disclosure.

Turning now to FIG. 5, another embodiment of a forceps provided in accordance with the present disclosure is shown generally identified by reference numeral 310. Forceps 310 is configured as a portable, battery-powered electrosurgical instrument and generally includes a housing 314, a battery assembly 318, an electrosurgical generator 328, a handle assembly 316, a rotating assembly 317, a shaft 312, a trigger assembly 330, an activation assembly 360, a drive assembly (not shown), and an end effector assembly 3100. Forceps 310 is similar to forceps 10 (FIG. 1) and may include any of the features of forceps 10 (FIG. 1) and/or forceps 210 (FIGS. 4A-4E).

Housing 314 of forceps 310 is configured to releasably engage electrosurgical generator 328 and battery assembly 318. That is, generator 328 is releasably engagable with body portion 315 of housing 314, while battery assembly 318 is releasably engagable with fixed handle portion 350 of housing 314. More specifically, battery assembly 318 is configured to engage fixed handle portion 350 of housing 314 such that battery assembly 318 functions as the stationary handle of housing 314 to facilitate grasping of the forceps 310. Generator 328 releasably engages body portion 315 of housing 314 and may be selectively removable from body portion 315 either in connection with the removal of battery assembly 318 or independently. Generator 328 is disposed in operable communication with battery assembly 318 to provide electrosurgical energy and control signals to forceps 310 for electrosurgically treating, e.g., sealing, and/or cutting tissue. Generator 328 may incorporate any of the features of and operate similarly to stand-alone generator "G" (FIG. 9), which will be detailed below with respect to FIG. 9.

Figure 6:
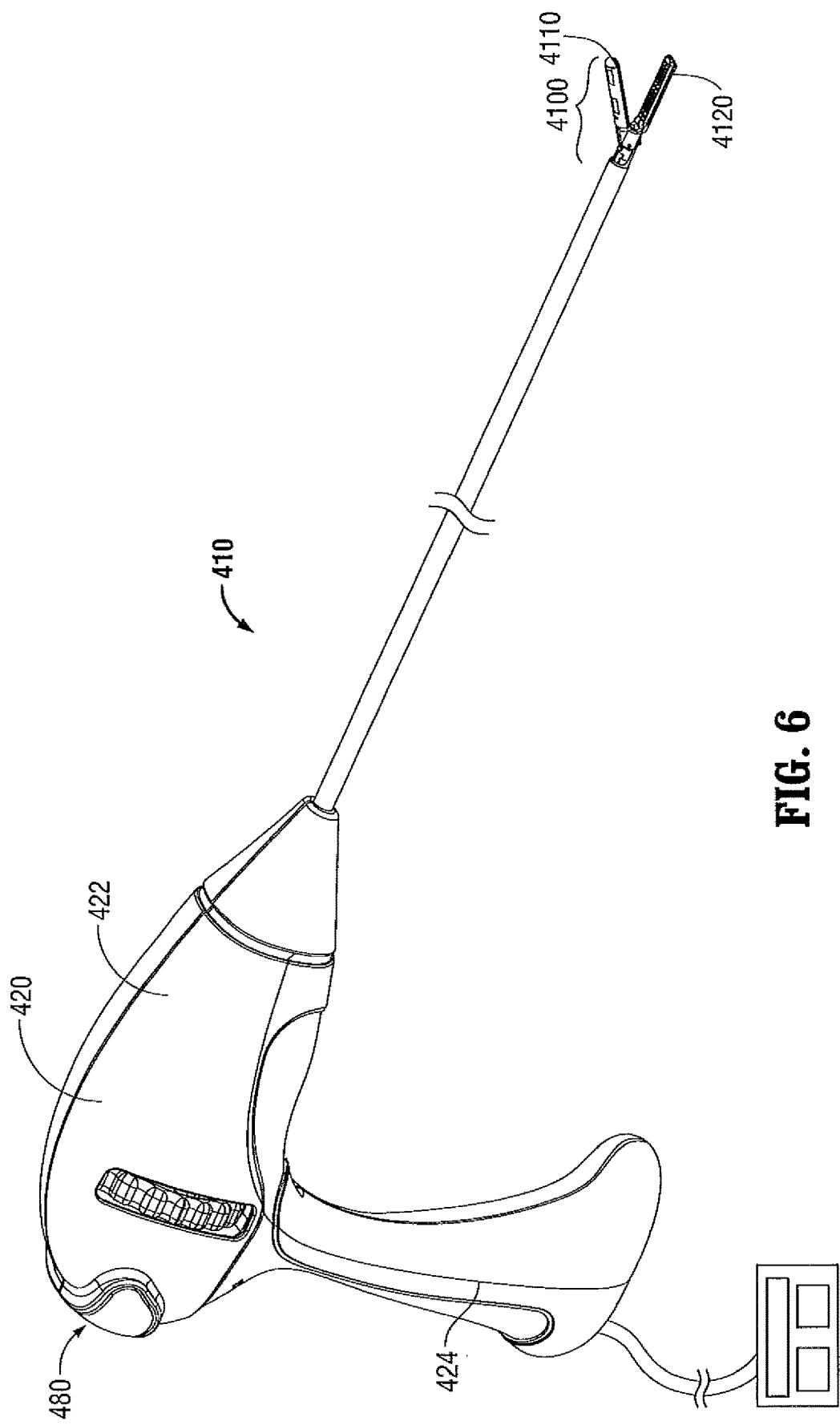
FIG. 6 is a perspective view of yet another surgical system provided in accordance with the present disclosure.

Referring to FIG. 6, another embodiment of a forceps provided in accordance with the present disclosure is shown generally identified by reference numeral 410. Forceps 410 is similar to forceps 10, 210 (FIGS. 1 and 4A, respectively) and may include any of the features thereof. Forceps 410 differs from the above embodiments in that forceps 410 is devoid of a movable handle and a trigger assembly, and, instead, simply defines a pistol grip-style housing 420 including a housing body 422 and fixed handle 424 to facilitate ergonomic grasping of forceps 410. Forceps 410 further includes a motor assembly (not shown, similar to motor assembly 160 (FIG. 2A)) disposed within housing 420 and configured for operating forceps 410, e.g., for grasping tissue between jaw members 4110, 4120 of end effector assembly 4100 and/or for advancing a mechanical cutting member (not shown) to cut tissue grasped between jaw members 4110, 4120. Alternatively, forceps 410 may be configured for electrical tissue cutting. An activation assembly 480 disposed on housing body 422 is configured for selectively initiating and deactivating forceps 410 and/or controlling operation thereof, e.g., controlling the motor assembly (not shown) and/or supply of energy to end effector assembly 4100.

Figure 7:
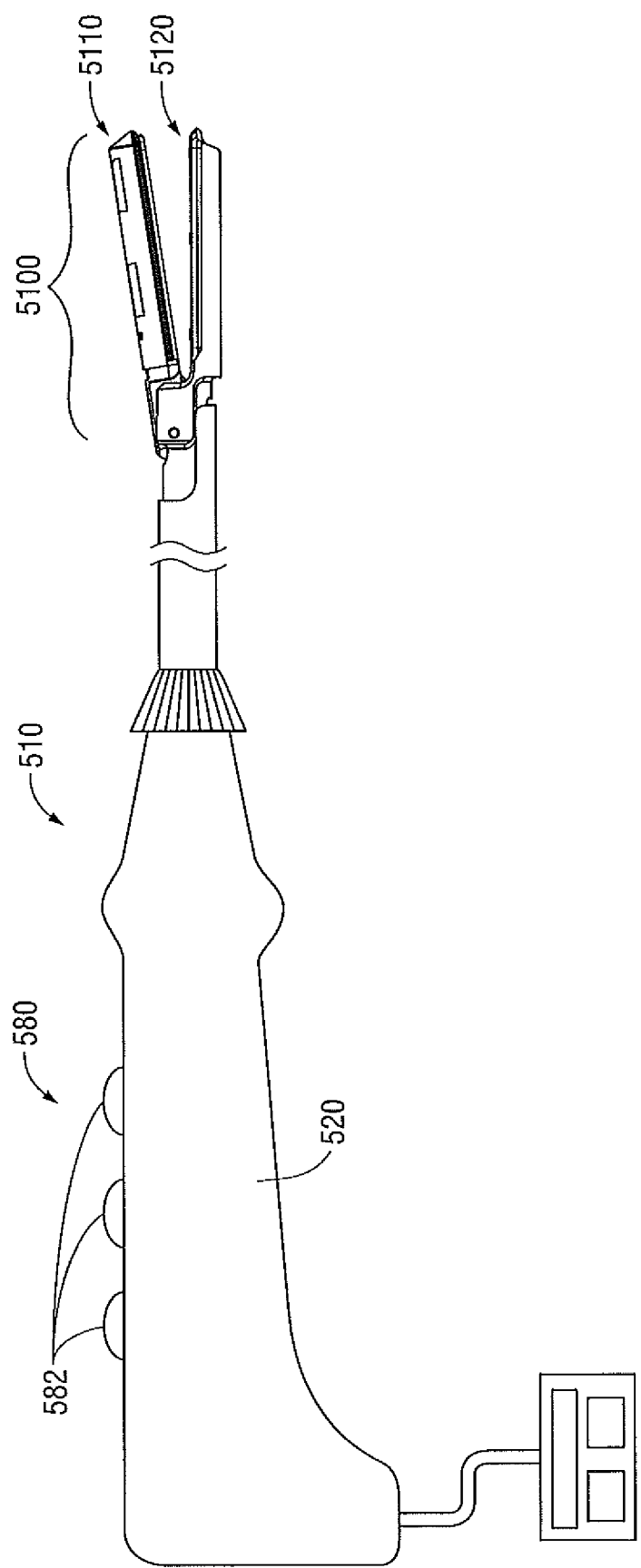
FIG. 7 is a side view of still another surgical system provided in accordance with the present disclosure.

FIG. 7 illustrates another embodiment of a forceps provided in accordance with the present disclosure and shown generally identified by reference numeral 510. Forceps 510 is similar to forceps 410 (FIG. 6) and may include any of the features of the above embodiments. Forceps 510 differs from forceps 410 (FIG. 6) in that, rather than providing a pistol grip-style housing 420 as in forceps 410 (FIG. 6), forceps 510 defines a straight-grip style housing 520 wherein housing 520 forms the grasping portion of forceps 510. Housing 520 includes an activation assembly 580 having a plurality of activation buttons 582 configured to activate, control, and/or deactivating forceps 510. Forceps 510 further includes a motor assembly (not shown, similar to motor assembly 160 (FIG. 2A)) disposed within housing 520 and configured for operating forceps 510, e.g., for grasping tissue between jaw members 5110, 5120 of end effector assembly 5100 and/or for advancing a mechanical cutting member (not shown) to cut tissue grasped between jaw members 5110, 5120, in embodiments where a mechanical cutter is provided.

Figure 8A:
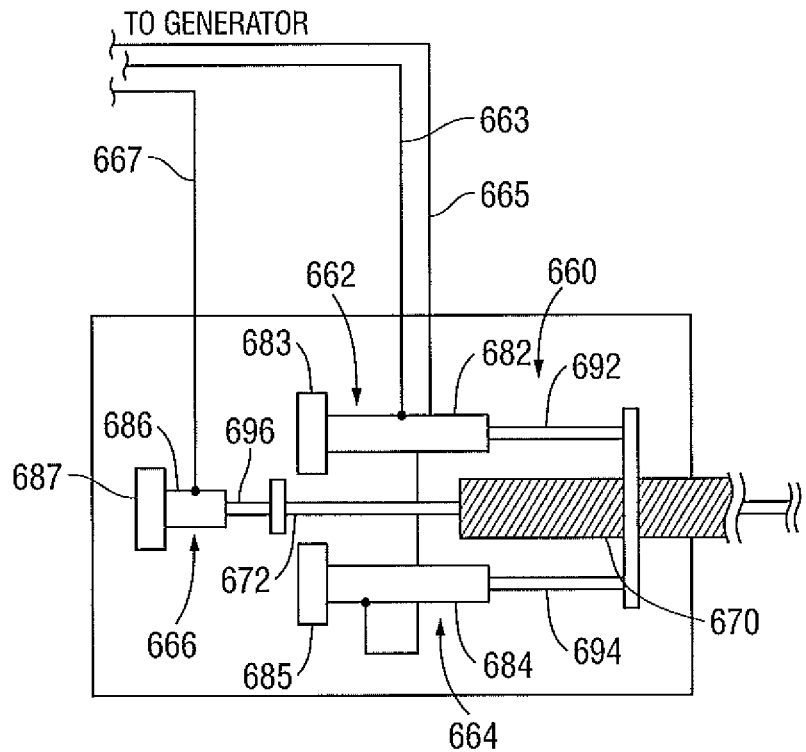
FIG. 8A is a longitudinal, cross-sectional view of a motor assembly provided in accordance with the present disclosure and configured for use with any of the above forceps.
Figure 8B:
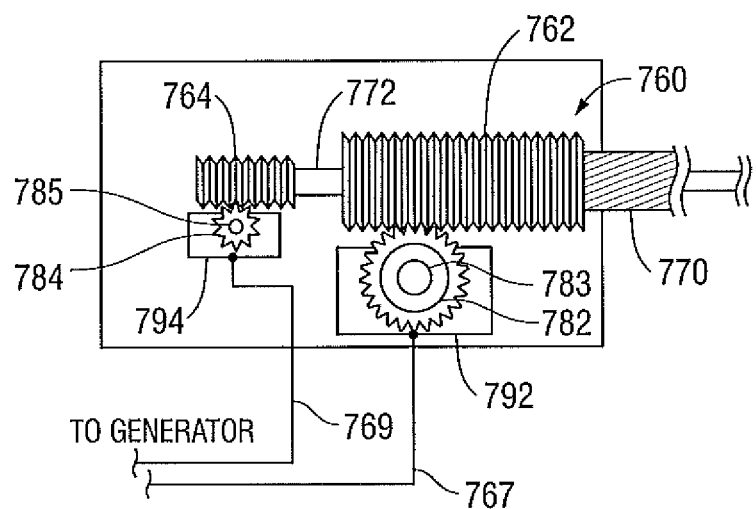
FIG. 8B is a longitudinal, cross-sectional view of another motor assembly provided in accordance with the present disclosure and configured for use with any of the above forceps.

Turning now to FIGS. 8A-8B, two embodiments of motor assemblies configured for use with any of the forceps described above, or any other suitable surgical instrument provided for use in accordance with the present disclosure, are shown generally identified by reference numerals 660 and 760, respectively. Motor assemblies 660, 760 are advantageous for use in the automatic mode of operation of the above-described forceps, e.g., wherein power and control signals from the generator selectively activate the motor assembly 660, 760 for manipulating the jaw members and/or mechanical knife assembly of the forceps. However, motor assemblies 660, 760 may also be operated via one or more actuation switches or buttons provided on the forceps and/or generator in the manual mode of operation.

Motor assembly 660, as shown in FIG. 8A, includes a plurality of linear actuators 662, 664, 666 coupled to generator "G" (FIG. 1) or other suitable power source via wires 663, 665, 667, respectively. Linear actuators 662 and 664 are coupled to drive bar 670 while linear actuator 666 is coupled to knife bar 672 (in embodiments where a mechanical cutting member is utilized, otherwise linear actuator 666 is not provided). Each actuator 662, 664, 666 includes a housing cylinder 682, 684, 686 coupled to a motor 683, 685, 687, and a respective shaft 692, 694, 696 slidably disposed within the housing cylinder 682, 684, 686 thereof. Shafts 692, 694, 696 are mechanically coupled to the drive bar 670 or knife bar 672, while housing cylinders 682, 684, 686 are fixed with respect to the housing of the forceps. Motors 683, 685, 687 coupled to housing cylinders 682, 684, 686 are electrically powered and controlled, e.g., via generator "G" (FIG. 1), for extending and retracting the respective shafts 692, 694, 696, thereby translating drive bar 670 or knife bar 672 to operate the end effector assembly of the forceps as detailed above. As an alternative to motors 683, 685, 687, housing cylinders 682, 684, 686 may be configured as pneumatic, hydraulic, or other suitable linear drive mechanisms configured to effect extension and retraction of shafts 692, 694, 696, respectively. As will be described in greater detail below, with respect to the automatic mode of operation, generator "G" (FIG. 1) may be utilized to control the operating parameters of linear actuators 662, 664, 666 for operating the end effector assembly based on user input and/or sensed feedback. In the manual mode of operation, on the other hand, user-activated controls may be utilized to control the operation of linear actuators 662, 664, 666.

Motor assembly 760, as shown in FIG. 8B, includes first and second cylindrical threaded members 762, 764 engaged to the respective drive bar 770 and knife bar 772. A gear member 782, 784 mounted on an axle 783, 785, respectively, is disposed in meshed engagement with each cylindrical threaded member 762, 764. A motor 792, 794 is coupled to each axle 783, 785 for rotatably driving the respective axle 783, 785 and, thus, the gear member 782, 784 thereof. Rotation of the gear members 782, 784, in turn, effects rotation and longitudinal translation of threaded members 762, 764 to thereby translate drive bar 770 and knife bar 772, respectively, to operate the end effector assembly of the forceps as detailed above. Motors 692, 694 are coupled to generator "G" (FIG. 1) and/or user-inputs via wires 767, 769, respectively, for electrically powering and controlling motor assembly 760.

Figure 9:
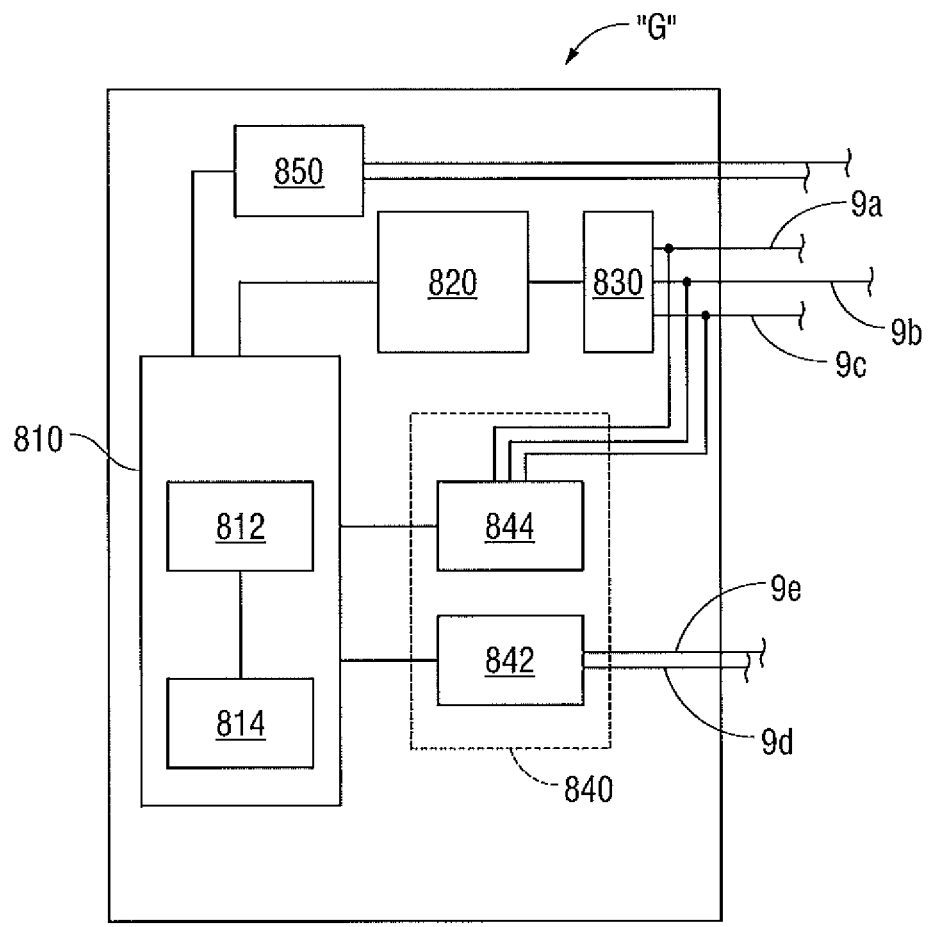
FIG. 9 is a schematic illustration of a generator assembly provided in accordance with the present disclosure and configured for use with any of the above surgical systems and/or forceps.

With reference to FIG. 9, in conjunction with FIGS. 1-2C, generator "G" is described for use with forceps 10 as part of surgical system 2. However, generator "G" may also be configured for use with any other suitable surgical instrument, such as the various embodiments of forceps provided herein. Generator "G," as mentioned above, is configured to both supply and control the supply of energy to end effector assembly 100 of forceps 10 for sealing and/or cutting tissue, and/or to control the operation of motor assembly 160 for manipulating end effector assembly 100, e.g., opening and closing jaw members 110, 120. In particular, in the manual mode, generator "G" provides feedback with respect to the configuration of end effector assembly 100 and the tissue sealing and/or tissue cutting processes while, in the automatic mode, generator "G" operates forceps 10 for grasping, sealing, and/or cutting tissue, via feedback-based control.

Generator "G" includes a controller 810, a high voltage DC power supply 820 (or other suitable power supply), an RF output stage 830 (or other suitable output depending on the energy delivered to end effector assembly 100), a sensor module 840, and a motor output module 850. Generator "G" may further include various input controls, e.g., buttons, activators, switches, touch screens, etc., for controlling generator "G." In addition, generator "G" may include one or more display screens for providing a variety of output information, e.g., intensity settings, treatment complete indicators, etc.

Controller 810 includes a processor 812 connected to a computer-readable storage medium or memory 814, which may be a volatile type memory, e.g., RAM, or a non-volatile type memory, e.g., flash media, disk media, etc. Controller 810 is coupled to power supply 820 and/or RF output stage 830, and motor output module 850, thus allowing processor 812 to control the output of the generator "G." In particular, power supply 820 and RF output stage 830, based on control signals received from processor 812 and/or user input, cooperate to selectively provide energy to tissue-contacting plates 114, 124 and/or cutting member 130, respectively, via wires 9a, 9b, and 9c, respectively, to seal and/or electrically cut tissue. Motor output module 850, on the other hand, provides power and control signals to motor assembly 160 for controlling end effector assembly 100, e.g., opening and closing jaw members 110, 120, and/or extending and retracting the mechanical knife (in embodiments where so provided). Processor 812 is further coupled to sensor module 840 for receiving feedback signals from sensor module 840 to perform feedback-based control of forceps 10. Memory 814 may store suitable instructions for indicating the sequence, duration, and/or parameters of the various actions controlled via controller 810.

Sensor module 840 includes a tissue presence unit 842 and a tissue property unit 844, although sensor module 840 may further include a plurality of other sensor units for measuring and providing feedback with respect to a variety of mechanical, tissue, and/or energy properties. Tissue presence unit 842 is coupled to tissue presence sensors 126, 128 of end effector assembly 100 via wires 9d and 9e and is configured to receive signals therefrom for determining the presence of tissue and/or the positioning of tissue disposed between jaw members 110, 120 when jaw members 110, 120 are disposed in the spaced-apart position, as detailed above, and for providing the same to controller 810. Tissue property unit 844 is coupled to wires 9a, 9b, 9c for sensing one or more properties of tissue grasped between jaw members 110, 120 during tissue sealing and/or tissue cutting and for providing the same to controller 810. In particular, tissue property unit 844 may be configured to sense the impedance of tissue (in addition to other properties such as temperature) grasped between jaw members 110, 120 during the conduction of energy between tissue-contacting plates 114, 124 and through tissue to monitor the tissue sealing process for determining when tissue sealing has been completed. Exemplary embodiments utilizing impedance-sensing during tissue sealing are described in U.S. Patent Application Pub. Nos. 2012/0283731 and 2013/0041367, and U.S. Pat. No. 8,034,049, the entire contents of each of which are incorporated by reference herein. Tissue property unit 844 may further be configured to sense the impedance of tissue grasped between jaw members 110, 120 during the conduction of energy between cutting member 130 and either or both of tissue-contacting plates 114, 124, e.g., during tissue cutting, to determine when tissue cutting has been sufficiently effected. An exemplary embodiment utilizing impedance-sensing during electrical tissue cutting is described in U.S. Pat. No. 7,270,664, the entire contents of which are incorporated by reference herein. Tissue property unit 844, provides the above-noted impedance (or other) data to controller 810.

As an alternative to generator "G," forceps 10 may include an onboard controller, motor output module, and sensor module that operate similar to the corresponding components of generator "G." In such an embodiment, forceps 10 need only be coupled to a generic energy supply that provides energy to forceps 10 for sealing and/or cutting tissue, while all the feedback based control of forceps 10 in the automatic mode of operation if effected via the onboard components of forceps 10.

Figure 10:
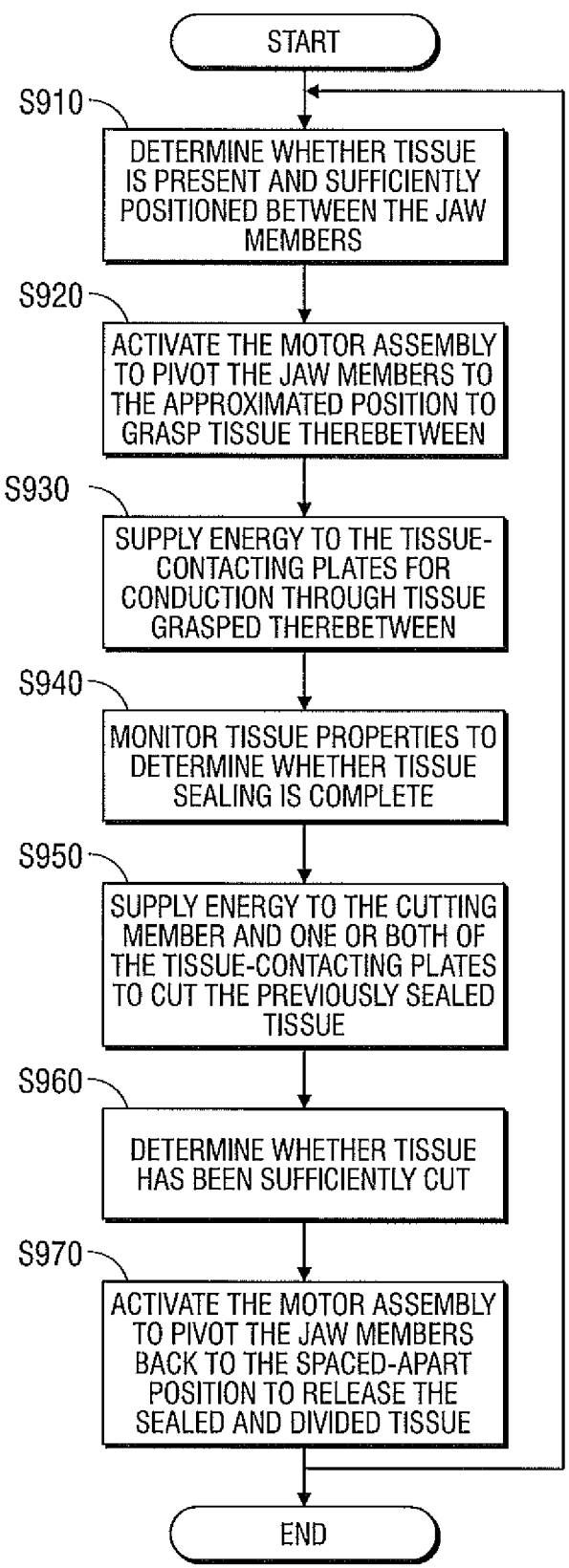
FIG. 10 is a flowchart outlining methods provided in accordance with the present disclosure.

Referring now to FIG. 10, in conjunction with FIGS. 1-2C and 9, the use of surgical system 2 in the automatic mode of operation is described, although the following description applies similarly to any of the other forceps detailed above or any other suitable surgical instrument and/or surgical system.

In order to activate forceps 10 for use in the automatic mode of operation, the user may actuate activation switch 82 of activation assembly 80, one or more inputs of generator "G", and/or move toggle member 92 to the automatic position. Once activated for use in the automatic mode of operation, end effector assembly 100 is manipulated into position such that tissue to be sealed and/or cut is disposed between jaw members 110, 120, with jaw members 110, 120 in the spaced-apart position. As indicated in step S910, with end effector assembly 100 positioned in the manlier noted above and forceps 10 activated in the automatic mode of operation, sensors 126, 128, in conjunction with generator "G," determine whether tissue is present and sufficiently positioned between jaw members 110, 120. If tissue is determined to be present and sufficiently positioned between tissue-contacting plates 114, 124 of jaw members 110, 120, the process proceeds to step S920.

In step S920, controller 810, based on the feedback from tissue presence unit 842 of sensor module 840 indicating that tissue is present and sufficiently positioned between tissue-contacting plates 114, 124 of jaw members 110, 120, signals motor output module 850 to activate motor assembly 160 for driving drive bar 142 distally to thereby effect movement of jaw members 110, 120 from the spaced-apart position to the approximated position to grasp tissue between tissue-contacting plates 114, 124. Once tissue is grasped between tissue-contacting plates 114, 124 of jaw members 110, 120, the process proceeds to step S930.

In step S930, with tissue grasped between tissue-contacting plates 114, 124, e.g., as determined by feedback provided to controller 810 by motor assembly 160, controller 810 signals power source 820 and/or RF output stage 830 to supply energy to tissue-contacting plates 114, 124 for conduction through tissue grasped therebetween to effect tissue sealing. During the application of energy to tissue-contacting plates 114, 124, as indicated in step S940, tissue property unit 844 of sensor module 840 monitors the impedance of tissue grasped between tissue-contacting plates 114, 124 (and/or other properties of tissue) to determine when an effective tissue seal has been established. Once an effective tissue seal has been established, the process proceeds to step S950.

In step S950, controller 810 signals power source 820 and/or RF output stage 830 to supply energy to cutting member 130 and/or tissue-contacting plates 114, 124 for conduction from cutting member 130 to either or both of tissue-contacting plates 114, 124 to electrically cut the previously sealed tissue. Alternatively, in embodiments where a mechanical knife is provided, such as in the embodiment of forceps 210 shown in FIGS. 4A-4E, controller 810 signals motor output module 850 to activate motor assembly 260 for driving knife bar 2186 distally to thereby effect movement of knife 2184 from the retracted position (FIG. 4D) to the extended position (FIG. 4E) to cut tissue grasped between jaw members 110, 120.

During the application of energy to cutting member 130 and/or tissue-contacting plates 114, 124, as indicated in step S960, tissue property unit 844 of sensor module 840 monitors the impedance of tissue grasped between cutting member 130 and tissue-contacting plates 114, 124 (and/or other properties of tissue or end effector assembly 100) to determine when tissue has been sufficiently cut. In embodiments where a mechanical cutter is provided, feedback provided to controller 810 by motor assembly 260 may indicate successful extension and retraction of knife 2184 to cut tissue (see FIGS. 4A-4E). Once tissue has been sufficiently cut, the process proceeds to step S970.

In step 970, once tissue has been effectively sealed and sufficiently cut, as detailed above, controller 810 signals motor output module 850 to activate motor assembly 160 for driving drive bar 142 proximally to thereby return jaw members 110, 120 back to the spaced-apart position to release the sealed and divided tissue.

Once the sealed and divided tissue has been released, end effector assembly 100 may be repositioned such that, once sensors 126, 128, in conjunction with generator "G," determine that tissue is present and sufficiently positioned between jaw members 110, 120, the above-described process repeats itself. As can be appreciated, such a configuration allows for rapid and repeated tissue sealing and cutting, which is particularly advantageous for use in advancing through large volumes of tissue.

It is also envisioned that surgical system 2 be capable of use in various combinations of the above-described automatic and manual modes of operation. That is, any of the operating steps of forceps 10 may be automatically initiated or manually activated to achieve a desired configuration. For example, grasping of tissue (and initiating the supply of energy to the jaw members) may be effected manually, while effecting (or completing) tissue sealing, effecting cutting (mechanically or electrically) of tissue, and releasing the sealed and cut tissue may be effected automatically. Other suitable combinations are also contemplated. Additionally, rather than effecting automatic actions, the above-described feedback based system may be utilized to indicate a current state of the process, for example, to indicate, e.g., via audible or visual indicators, that tissue is present between the jaw members, tissue sealing is complete, and/or that tissue cutting is complete.

The various embodiments disclosed hereinabove are particularly advantageous for use with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include, remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions. In particular, the robotic system may operably communicate with generator "G" such that the so-called "manual" operations of forceps 10 are performed via the robotic system and/or under control of generator "G." Alternatively, the robotic system may be fully integrated with generator "G" such that a fully automatic surgical procedure may be effected, under the guidance and/or selectively control of a remote surgeon.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system, comprising:
    an end effector assembly including first and second jaw members;
    at least one tissue presence sensor disposed at the end effector assembly;
    a motor assembly coupled to the end effector assembly and operable to move the jaw members between a spaced-apart position and an approximated position for grasping tissue therebetween;
    an energy source coupled to the end effector assembly and operable to supply energy to the jaw members to seal tissue; and
    a controller including a processor and a non-transitory computer-readable storage medium storing a control program that, when executed, causes the processor to:
    activate the motor assembly, once the controller determines that tissue is present between the jaw members based on information received from the at least one tissue presence sensor, to move the jaw members from the spaced-apart position to the approximated position to grasp tissue;
    activate the energy source, once tissue is grasped between the jaw members, to supply energy to the jaw members to seal tissue grasped between the jaw members; and
    activate the motor assembly, once the controller determines that tissue sealing is complete, to move the jaw members from the approximated position to the spaced-apart position to release sealed tissue.

2. The system according to claim 1, further comprising:
    a forceps having the end effector assembly disposed at a distal end thereof; and
    a generator containing the energy source and the controller, the generator operably coupled to the forceps.

3. The system according to claim 2, wherein the generator is incorporated into a housing of the forceps.

4. The system according to claim 1, further comprising at least one tissue property sensor coupled between the end effector assembly and the energy source and configured for sensing at least one tissue property indicative of completion of tissue sealing, the at least one tissue property sensor coupled to the controller for enabling the controller to determine whether tissue sealing is complete.

5. The system according to claim 4, wherein the at least one tissue property is tissue impedance.

6. The system according to claim 1,
    wherein the end effector assembly further includes a cutting member,
    wherein the energy source is coupled to the cutting member and operable to supply energy to the cutting member for conduction between the cutting member and at least one of the jaw members and through tissue grasped between the jaw members to cut tissue,
    wherein the control program further causes the processor to activate the energy source, once it is determined that tissue sealing is complete, to supply energy to the cutting member to cut sealed tissue, and
    wherein activating the motor assembly to move the jaw members from the approximated position to the spaced-apart position to release tissue is effected once it is determined that both tissue sealing and tissue cutting are complete.

7. The system according to claim 1,
    wherein the end effector assembly further includes a knife movable between a retracted position, wherein the knife is disposed proximally of the jaw members, and an extended position, wherein the knife extends between the jaw members to cut tissue disposed therebetween,
    wherein the motor assembly is coupled to the knife and operable to move the knife between the retracted position and the extended position,
    wherein the control program further causes the processor to activate the motor assembly, once tissue sealing is complete, to move the knife from the retracted position to the extended position to cut sealed tissue, and
    wherein activating the motor assembly to move the jaw members from the approximated position to the spaced-apart position to release tissue is effected once it is determined that tissue sealing is complete and once tissue cutting is complete.

8. A surgical system, comprising:
    an end effector assembly including first and second jaw members;
    at least one tissue presence sensor disposed at the end effector assembly;
    a knife assembly including a knife movable relative to the end effector assembly;
    a motor assembly coupled to the end effector assembly and the knife assembly, the motor assembly operable to move the jaw members between a spaced-apart position and an approximated position for grasping tissue therebetween, and operable to move the knife relative to the end effector assembly between a retracted position, wherein the knife is disposed proximally of the jaw members, and an extended position, wherein the knife extends between the jaw members to cut tissue disposed therebetween;
    an energy source coupled to the end effector assembly and operable to supply energy to the jaw members to seal tissue; and
    a controller configured to:
        determine whether tissue is present between the jaw members based on information received from the at least one tissue presence sensor and activate the motor assembly when the controller determines that tissue is present between the jaw members to move the jaw members from the spaced-apart position to the approximated position to grasp tissue between the jaw members;
        activate the energy source to supply energy to the jaw members to seal tissue grasped between the jaw members;
        determine whether tissue sealing is complete and activate the motor assembly when the controller determines that tissue sealing is complete, to move the knife from the retracted position to the extended position to cut tissue sealed tissue grasped between the jaw members; and
        activate the motor assembly to move the jaw members from the approximated position to the spaced-apart position to release sealed and cut tissue.

9. The system according to claim 8, further comprising:
a forceps having the end effector assembly disposed at a distal end thereof; and
a generator containing the energy source and the controller, the generator operably coupled to the forceps.

10. The system according to claim 9, wherein the generator is incorporated into a housing of the forceps.

11. The system according to claim 8, further comprising at least one tissue property sensor coupled between the end effector assembly and the energy source and configured for sensing at least one tissue property indicative of completion of tissue sealing, the at least one tissue property sensor coupled to the controller for enabling the controller to determine whether tissue sealing is complete.

12. The system according to claim 11, wherein the at least one tissue property is tissue impedance.

\* \* \* \* \*